United States Patent [19]

Maness et al.

[11] Patent Number: 4,734,034
[45] Date of Patent: Mar. 29, 1988

[54] CONTACT SENSOR FOR MEASURING DENTAL OCCLUSION

[75] Inventors: William L. Maness; Robert F. Golden; Michael H. Benjamin; Robert M. Podoloff, all of Boston, Mass.

[73] Assignee: Sentek, Incorporated, Cambridge, Mass.

[21] Appl. No.: 717,532

[22] Filed: Mar. 29, 1985

[51] Int. Cl.$^4$ ............................................. A61C 19/04
[52] U.S. Cl. .................... 433/68; 73/865.7; 128/777; 338/99; 340/665; 433/71
[58] Field of Search ............................ 433/68, 69, 71; 128/777, 774, 776, 782; 73/781, 776, 790, 818, 172, 379, 432 T; 340/665, 666; 338/99

[56] References Cited

U.S. PATENT DOCUMENTS

| | | | |
|---|---|---|---|
| 2,951,817 | 9/1960 | Myers | 252/511 |
| 3,349,489 | 10/1967 | Shackelford | 433/68 |
| 3,503,031 | 3/1970 | Nyhus et al. | 338/99 |
| 4,155,262 | 5/1979 | Wong et al. | 338/4 |
| 4,208,648 | 6/1980 | Naumann | 338/99 |
| 4,301,337 | 11/1981 | Eventoff | 200/5 A |
| 4,314,228 | 2/1982 | Eventoff | 338/99 |
| 4,319,078 | 3/1982 | Yokoo et al. | 338/99 |
| 4,402,326 | 9/1983 | Okano et al. | 433/68 |
| 4,451,714 | 5/1984 | Eventoff | 338/99 |
| 4,488,873 | 12/1984 | Bloomfield et al. | 433/71 |
| 4,492,949 | 1/1985 | Peterson et al. | 338/99 |
| 4,521,186 | 6/1985 | Wodlinger et al. | 128/777 |
| 4,529,959 | 7/1985 | Ito et al. | 338/99 |
| 4,555,953 | 12/1985 | Dario et al. | 73/432 T |

OTHER PUBLICATIONS

"A Force Transducer Employing Conductive Silicon Rubber", J. A. Purbrick, Apr. 1981, First Robot Vision and Sensors Conference.

"Active Touch Sensing", W. D. Hillis, Apr., 1981, Massachusetts Institute of Technology, A. I. Memo 629.

Primary Examiner—John J. Wilson
Attorney, Agent, or Firm—Wolf, Greenfield & Sacks

[57] ABSTRACT

A contact sensor for detecting points on a grid where the sensor is being contacted on opposing sides by teeth surfaces or other contacting points. The contact sensor includes two sets of parallel electrodes which are each formed of a thin, flexible supporting sheet. The electrodes are coated with a thin, resistive coating. Two such electrode structures are oriented at approximately right angles to create a grid where the intersecting electrodes cross separated by the resistive coatings. The resistive coatings may be made from conventional resisitive inks and are optionally separated by a separation material, such as talcum or mesh. In the absence of an external force, the material between the electrodes sets provides a high resistance between intersecting electrodes. The novel composition of the intermediate layer results in a structure which provides a "switching" effect such that the resistance between electrodes is very high where there is no external pressure and changes to a comparatively low value at locations where external pressure is applied by two contacting points or surfaces. The sensor output is dynamic in the sense that the resistance will change back and forth between high and low resistance states as external pressure is repeatedly applied and removed. The sensor may be made extremely thin and can provide high resolution capable of distinguishing between contact points separated by 0.050 inches or less.

Additionally, the sensor output may be provided by means of a small computer or similar digital processor which monitors the signals from the sensor grid and which provides an output which indicates the variation in contacting points with time.

23 Claims, 9 Drawing Figures

CONTACT SENSOR FOR MEASURING DENTAL OCCLUSION

FIELD OF THE INVENTION

This invention is related to the field of contact sensors, and more particularly to the field of dental occlusal sensors for providing measurements of dental contact points as a patient's jaw is closed.

BACKGROUND OF THE INVENTION

It is frequently desirable or necessary in performing dental diagnostic procedures to measure the occlusion, or points of contact, between a patient's teeth as the patient closes his or her jaws. Occlusion measurements are necessary in prescribing and fitting many dental appliances such as false teeth or orthodontic devices. Such measurements enable the user to determine where the teeth first contact each other, disclosing high spots and other useful information.

In order to provide an accurate measurement of the occlusion, an occlusal measuring device must be extremely thin so as not to perturb the normal dental alignment. A sensor must also have a very high resolution to provide useful information and distinguish between contact and non-contact points of the teeth. Additionally, a practical sensor must be safe for oral use and should be capable of being used by non-technical personel with minimal training.

To date, the types of occlusal sensors available to dentists for measuring occlusion have been limited. The most common method of measuring dental occlusion is by means of a piece of carbon-paper like material upon which a patient bites down. The points of contact are indicated by the deposit of a marking substance on the dental surfaces. This method is rapid to use and inexpensive, but provides limited information. The resolution is not very great, especially where complex dental interactions are involved, and there is no easy method to retain a permanent record in a patient's files for later comparison.

Another occlusal sensor uses a thin piece of plastic which is bitten to provide an imprint of the occlusion. The occlusion is read by illuminating the plastic with polarized light which indicates the points of contact by different colors. Disadvantages of this method include a relatively thick sensor, a high degree of training necessary to interpret the results, and a relatively complex procedure to create the imprint pattern.

Other methods exists for performing occlusal analysis, including X-rays and casts of a patient's bite, but these methods are expensive, time consuming, and in general are not suitable for large scale use in dental offices. A simple and inexpensive method of providing occlusal measurements which have a high resolution and which are capable of being permanently retained would be of great value to dentists and others concerned with occlusal measurements.

SUMMARY OF THE INVENTION

The present invention includes a unique contact sensor for detecting points on a grid where the sensor is being contacted on opposing sides by teeth surfaces. The sensor is extremely thin, on the order of a few thousands of an inch thick, and can provide high resolution capable of distinguishing between contact points seperated by 0.050 inches or less.

Briefly, the contact sensor includes two sets of parallel electrodes which are each formed on a thin, flexible supporting sheet. The electrodes are then coated with a thin, resistive coating. Two such electrode structures are oriented at approximately right angles to create a grid where the intersecting electrodes cross. The electrodes are then formed into a sheet with the electordes being seperated by a novel intermediate layer.

In the absence of an external force, the intermediate layer provides a high resistance between intersecting electrodes. The novel composition of the intermediate layer results in a structure which provides a "switching" effect such that the resistance between electrodes is very high where there is no external pressure and changes to a comparatively low value at locations where external pressure is applied by two contacting points or surfaces. The sensor output is dynamic in the sense that the resistance will change back and forth between high and low resistance states as external pressure is repeatedly applied and removed. Thus, repeated measurements of contacting points may be made by a single sensor.

Although the contact sensor has many possible applications, it is ideally suited for measuring dental occlusion. The extreme thinness of the sensor allows occlusion to be measured with little or no alteration of a patient's normal bite, and the high resolution provides detailed information to a dentist or other user about the interaction of dental surfaces. The binary switching action of the inter-electrode resistance allows simple circuitry to reliably detect contacting and non-contacting points of a patient's teeth as the sensor is bitten and contact is made between the teeth. The sensor may be fabricated very inexpensively. This allows a sensor to be discarded after use by one patient, thus eliminating the necessity of sterilization between patients.

Additionally, the sensor output may be provided by means of a small computer or similar digital processor which monitors the signals from the sensor grid and which provides an output which indicates the variation in dental occlusion with time. Since multiple contacts may be measured at each electrode intersection, the changing patterns of dental occlusion as a patients bites down on the sensor can be monitored to provide a total representation of the patient's occlusion as the jaw is closed. This information is extremely valuable in diagnosing and treating certain dental problems. The ability to take such measurements quickly and to keep a permanent record of the occlusion is valuable in providing later follow up care.

DESCRIPTION OF THE DRAWINGS

The invention may be more fully understood by reading the following description of the preferred embodiment in conjunction with the accompanying drawings, of which.

DESCRIPTION OF THE PREFERRED EMBODIMENT

Figure 1:
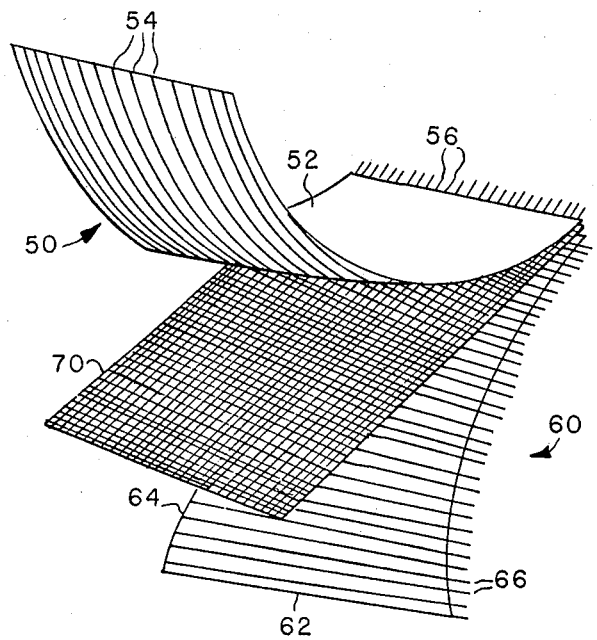
FIG. 1 shows the overall construction of the sensor of the invention.

Referring to FIG. 1, the basic structure of the contact sensor used in the present invention is shown. A top layer 50 is fabricated as discussed in detail below. Top layer 50 includes a flexible backing 52 on which are formed parallel rows of electrodes 54. Each electrode is connected to a respective terminal 56 through which electrical contact to the electrode is made. A bottom layer 60 is similarly constructed and includes multiple electrodes 64 fromed on a backing 62 and respectively connected to terminals 66. A seperation layer 70 is normally included between the top and bottom layers 60 and 70.

Figure 2:
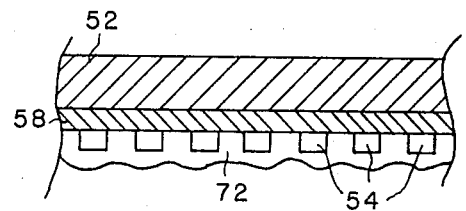
FIG. 2 shows a magnified view of the relationship of the electrodes to the backing and resistive coating.

Referring to FIG. 2, the construction of the top and bottom layers is shown in more detail. The backing 52 provides a flexible support for electrodes 54. In the preferred embodiment described herein, backing 52 is formed of a polyester film such as Mylar. Other similar films such as Kapton, manufactured by DuPont, may be used for the backing. These materials combine thinness and strength in a material which can be made into a sterile, waterproof package suitable for oral use. Other materials may be used for the backing.

In the preferred embodiment, electrodes 54 are formed via know methods for making flexible printed circuits. A thin copper layer is attached to the backing 52 with an adhesive 58. The electrode pattern is applied to the copper layer with photo-resist, and the unwanted copper is then etched away. Other methods may be used to fabricate the electrodes including directly printing the electrodes on the backing using a conducting ink.

Next, the electrodes are coated with a resistive coating 72. Coating 72 may be formed of a resistive ink. Resistive inks are materials which can be printed or otherwise applied in thin coatings and which serve to limit the current flowing therethrough. The technology of formulating and applying resistive inks is well developed. See, for example, *Screen Printing Electronic Circuits*, by Albert Kasoloff, 1980, and National Bureau of Standards Circular No. 530, U.S. Government Printing Office.

In the preferred embodiment, a resistive coating is used which includes graphite in an acetone or keytone solvent. The resistive coating should be applied in as thin a layer as possible. The preferred thickness is in the range of ½ to 2 mils thick. In the preferred embodiment described below, the resistive coating is formed by combining an insulating ink having a titanium dioxide filler, vinyl resin binder, and butyl cellosolve acetate solvent with a conductive ink containing graphite, vinyl resin, and butyl cellosolve acetate. Such inks are commercially available from many sources, e.g., Electrodag 423SS conductive ink and SS 24210 insulating ink, produced by Acheson Colloids Company, Port Huron, Mich. The resistance of the coating can be varied by changing the relative proportions of the insulating and conductive components of the coating. In the preferred embodiment, the coating is composed of the above-described formation having twenty percent conductive and eighty percent insulative inks by weight. The coating is applied through a 200 mesh polyester screen and room dried. The coating is preferably one-half mil thick with a resistivity of 60 to 100 kilohms per square.

To form the sensor, two layers as shown in FIG. 2 are placed together with the electrodes at angles to each other, as shown in FIG. 1, in a sandwich arrangement with the resistive coatings 72 facing one another and optionally seperated with a seperation layer 70, as discussed below.

It has been discovered that a sensor constructed in accordance with the procedure set forth above has the characteristic that the resistance between electodes as a function of applied pressure is non-linear. Application of an external force has minimal effect on the resistance between opposing electrodes at the pressure point until a threshold point is reached, at which point the resistance between the opposing electrodes abruptly decreases. For the sensor and resistive coating formation described above, the resistance changes from a value on the order of several megohms to a value on the order of one kilohm. As a result of this phenomenon, the described sensor may be used to detect contacting points using relatively simple circuitry while maintaining a very high signal to noise ratio in the output.

When two electrode layers such as that shown in FIG. 2 are combined in a sensor with the resistive coatings 72 in direct contact, it has been found that the threshold force required to switch from the high resistance state to the low resistance state is variable, resulting in possible spurious readings. A seperation layer 70, as shown in FIG. 1, may be added to the sensor to improve its performance. The primary requirements of the seperation layer are that it be non-conductive, flexible, and as thin as possible. Various materials may be used as the seperation layer. Materials which have been used and found suitable include nylon mesh, non-conducting paints including polymer-based paints such as Acheson Electrodag SS24210 or latex paint, and talcum powder.

Of these materials, talcum powder has provided the best results. In use, a thin layer of talcum powder is applied to both of the resistive coatings. The excess talcum powder is removed with a low velocity stream of air, such as by blowing off the powder, the powder remaining providing the seperation layer. Nylon mesh has also prove to be useful as a seperation layer. Nylon mesh reults in a higher threshold force to switch the interelectrode resistance from high to low resistance states, however using such a mesh tends to decrease the ability of the sensor to accurately detect continuous lines or surfaces of contact.

Figure 3:
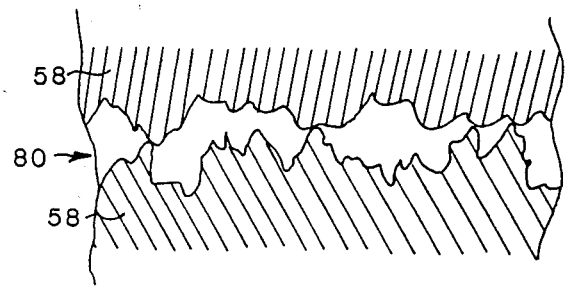
FIG. 3 is a microscopic view of the interface between resistive coatings on facing electrode arrays.

While the reason for the switching effect described above has not been precisely determined, the following is believed to be the explanation. The resistive coating, when applied, has a gritty surface. When two electrode layers are combined wit the resistive coatings facing one another, the structure is believed to have the configuration shown in FIG. 3. In FIG. 3, the two resistive layers 58 contact each other along an interface 80. Due to the grittiness of the surface, the contacting area is very small with only isolated high points of the opposing coatings 58 actually touching. When pressure is applied, the coating elastically deforms creating a larger area of contact and a lower resistance. It is believed that the threshold effect is at least partially due to the need to overcome the starting frictional forces which resist any sliding action between the two coatings until a threshold level is exceeded. It is further believed that the seperation layers serve to provide a more constant interface between the two layers, thus providing for a more even threshold force level.

The above described sensor also works when only the resistive coating is applied to only one of the electrode arrays, although the sensor sensitivity is more variable than with the construction using two coatings. A seperation layer may optionally be used on top of the resistive coating, and such a seperation layer reduces the variability of the threshold force, similarly to the two coating sensor. Using two coatings is preferred, however.

The sensor of the present invention is capable of very high resolution. Sensors have been built in accordance with the above procedure which have electrode spacings of 0.050 inches. The principal factor limiting resolution is the capability of available methods to form thin electrode grids. The smallest electrode spacing which can now be reliably achieved using conventional printed circuit or conductive ink deposition methods is approximately 0.010 inches. Finer resolution would appear to be achievable.

Figure 8A:
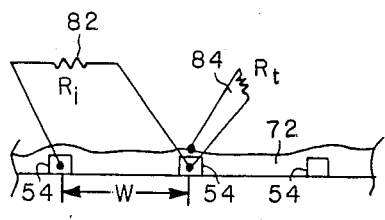
FIGS. 8A and 8B are useful in estimating the through and inter-electrode resistances of a sensor array for different electrode spacings.

Referring to FIG. 8A, the inter trace resistance $R_i$ of the resistive coating 72 between electrodes is represented by resistor 82. The through resistance $R_t$ from each electrode to the surface is represented by resistor 84. The seperation between electrodes is W.

Figure 8B:
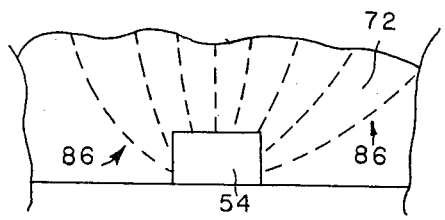

The resistance through a specific configuration is inversely proportional to the cross-sectional area and proportional to the length through which the current flows. The through resistance $R_t$ depends upon the total surface area through which a current flows. The pattern of this current flow is illustrated in FIG. 8B by dotted current lines 86 from electrode 54 to the surface of the resistive coating 72. The nature of this flow makes the through resistance difficult to calculate analytically. From experimental measurements, however, it is known that this resistance is on the order of a few thousand ohms.

The inter-electrode resistance $R_i$ is easier to calculate since the length of the resistive path is long compared to the cross-sectional area resulting in a generally linear current flow. Thus, the inter-electrode resistance may be expressed as $$R_i = K_c \times \frac{W}{A}$$

where $K_c$ is a proportionality constant, A is the cross-sectional area of the resistive coating between traces, and W is the electrode seperation. For an electrode spacing of 0.050 inches and using the electrode and sensor structure described above, $R_i$ is above five megohms. From the above equation, the interelectrode resistance is proportional to W. Reducing W by a factor of ten to 0.005 inches will result in a value of $R_t$ on the order of 500 kilohms. Thus, the inter-electrode resistance will still be much larger that the through resistance for electrode spacings of 0.005 inches, which is finer than can be achieved with conventional processes.

Figure 4:
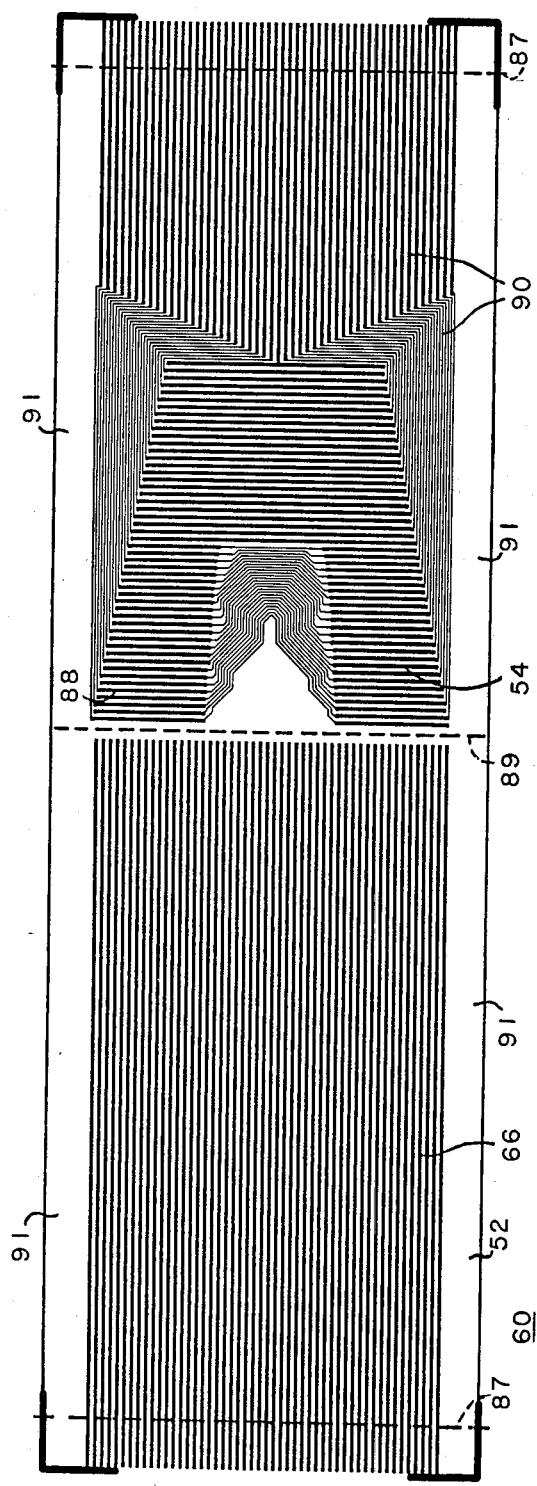
FIG. 4 shows one method by which a dental occlusal sensor may be fabricated as a single piece.

A practical sensor for use in dental applications should preferably be disposable to eliminate the need for sterilization between patients. FIG. 4 shows the configuration for an electrode layer in which the top and bottom electrode arrays are simultaneously formed on a single backing sheet. In FIG. 4, a backing sheet 52 has column electrodes 66 formed on one half thereof and row electrodes 54 formed on the other half. The row electrodes have an area 88 where the teeth make contact with each other from opposite sides of the sensor. Conductive paths 96 are in the area between the contacting surfaces of the teeth and serve to connect row electrodes 88. The row and column electrodes extend to either end of the sheet 52 where a connector is attached at the regions denoted by dottet lines 87 to provide electric contact to the electrodes. The electrodes 90 connect row electrodes 54 to the connector region 87.

After the electrodes are formed, the structure shown in FIG. 4 has a resistive coating and optional seperation layer applied thereto, as described above. The backing sheet 52 is then folded at line 89 so that the row and column electrodes face one another, and the structure thus formed is held together by applying an adhesive or tape to the edge portions 91 of the folded sensor.

Figure 5:
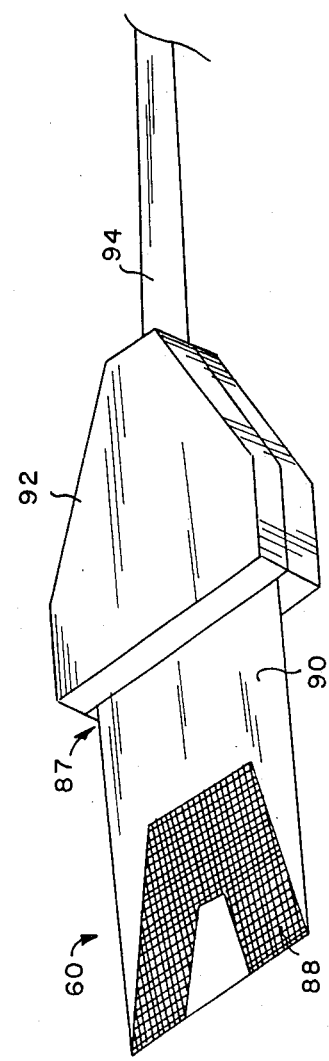
FIG. 5 shows an exemplary structure for oral use of an occlusal sensor.

To make a dental occlusal sensor, the sensor shown in FIG. 4 may be fabricated into a configuration suitable for oral use, such as that shown in FIG. 5. In FIG. 5., the sensor 60 is shown with the electrode area 88 crosshatched to indicate where a patient would bite down on the sensor. The signals from the sensor are applied to the measurement electronics via a multiconductor cable 94 which is attached to the sensor via a connector 92. Signals from the electrodes in area 88 are applied to the connector 92 via conductors within the supporting sheet 90, as described above with reference to FIG. 4. Connector 92 may make contact directly to the electrode traces 87 on the sensor 60 without the necessity for having a matching connector piece attached to the sensor. in this manner, an inexpensive oral sensor may be easily fabricated, allowing for the use of disposable sensors. This greatly increases the ease of use, since sterilization between patients is not required, and also reduces the posibility of transmission of germs due to incomplete sterilization of sensors between uses.

Figure 6:
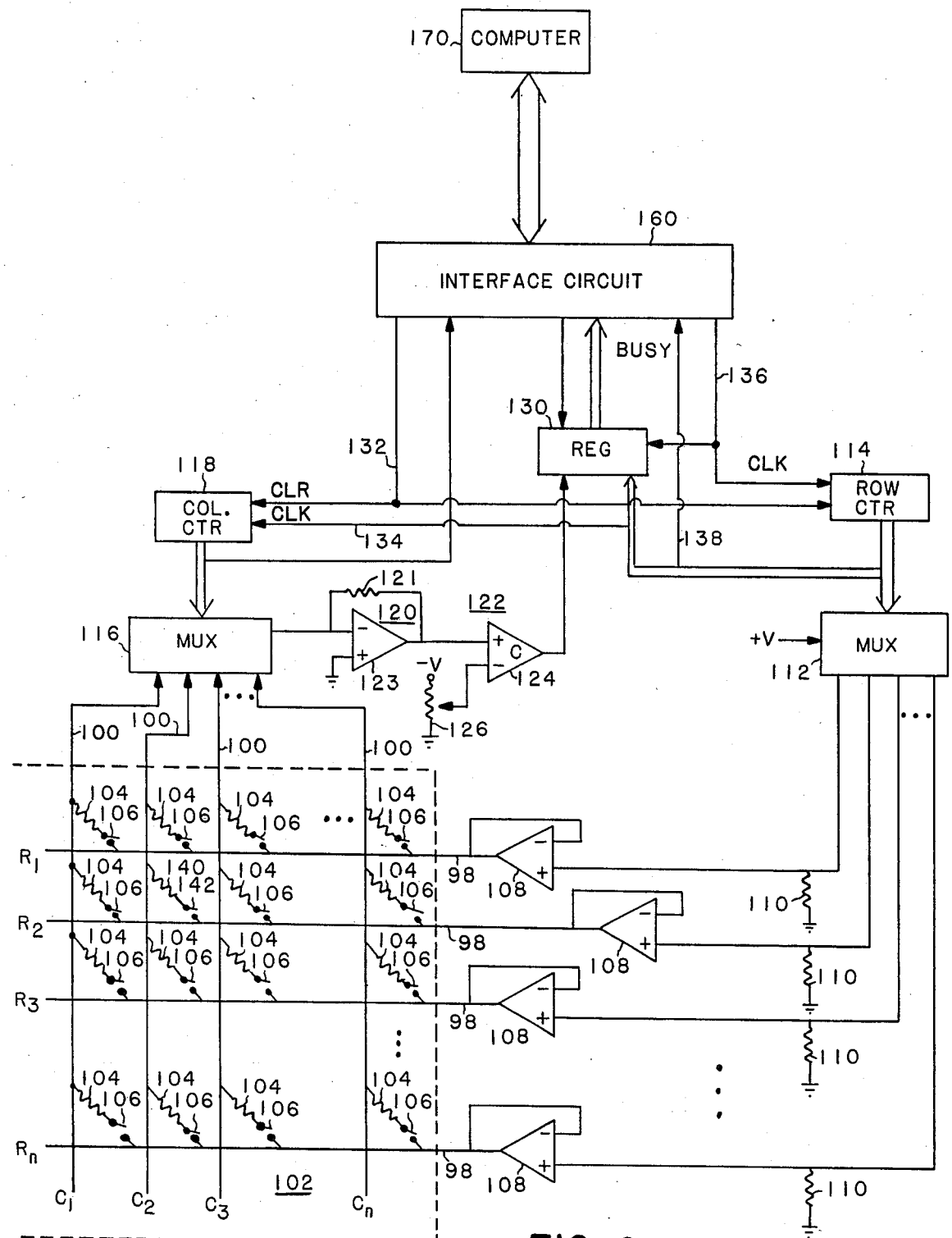
FIG. 6 shows circuitry for measuring the resistance of electrode array points in a sensor.

Referring to FIG. 6, a circuit is shown for reading the sensor output in conjuction with a personal computer. It should be appreciated that a dedicated digital controller or other type of processor could equally well be used in place of the computer, and the use of such alternate processors may be preferrable in some applications. In the preferred embodiment, computer 170 is an IBM Personal Computer which is interfaced to the circuitry shown through an interface circuit 160. The design of interface 160 will be readily apparent to one of ordinary skill in the art. An example of such an interface circuit which will work with the IBM PC is shown and described in the *IBM PC Technical Reference Manual*, Vol. 2, at pages "prototype card 9."

In FIG. 6, a sensor 102 includes of a plurality of column electrodes 100, designated as $C_1$ through $C_n$, and a plurality of row electrodes 98, designated as $R_1$ through $R_n$. In the preferred embodiment, the sensor includes 48 rows and 48 columns. At each intersection of a row and column is a resistor 104 and switch 106. Resistors 104 have a resistance on the order one kilohm. The plurality of resistors 104 represent the low resistance between opposing electrodes when contact is detected. The closing of switches 106 represents the switching from a high to low resistive state of the interelectrode resistance by the closing of the corresponding switch 106. Ech intersection has a measureable resistance of several megohms, not represented in FIG. 6, in the absence of contact at that intersection.

Each row electrode is driven by the output of an asociated amplifier 108, shown in FIG. 6 as unity gain buffer amplifiers. The input to each amplifier 108 is connected to ground through a resistor 110 and also to an output from multiplexer 112. The common terminal terminal of multiplexer 112 is connected to a positive voltage +V.

Normally, the inputs to amplifiers 108 are held at ground porential by resistors 110. As described below, in response to digital inputs from row counter 114, multiplexer 112 sequentially connects the inputs to each row-driver amplifier 108 to the +V potential, causing the corresponding row electrode to also go to a high potential. Row counter 114 is incremented by a clock signal from interface circuit 160, as described in more detail below.

Each of the column electrodes is connected to an individual input to a 48-to-1 multiplexer 116. Column counter 118 is incremented by a carry signal from row counter 114 after all the points along each row have been measured. In response to inputs from a column counter 118, multiplexer 116 sequentially connects each column electrode to the input to an amplifier circuit 120.

Amplifier 120 includes an op-amp 123 and feedback resistor 121. The non-inverting input of op-amp 120 is grounded, and feedback resistor 121 is connected from the op-amp output to the inverting input. Thus, the inverting input to the op-amp is a virtual ground, and the voltage at the output of the op-amp is a function of the current flowing into the inverting input. Amplifier 120 is connected as an inverting amplifier.

The output signal from amplifier 120 is applied to a threshold detector 122, including a comparator 124 and a potentiometer 126. Comparator 122 provides a digital signal to a register 130, depending on whether the output voltage from amplifier 120 is above or below the threshold level selected by potentiometer 126, as discussed below.

The measurement circuit operates in the following manner. Assume that the circuitry has selected column $C_2$ and row $R_2$, which will measure the resistance of the electrode intersection represented by resistor 140 and switch 142. Counter 114 and multiplexer 112 apply a high voltage to row electrode $R_2$ via the corresponding amplifier 108. All other row electrodes are held at ground potential by their corresponding amplifiers 108.

Multiplexer 116 connects column electrode $C_2$ to comparator 122 via amplifier 120. Since the input to the amplifier 120 is a virtual ground and all the row electrodes except except the selected electrode $R_2$ are held at or close to ground potential, no current can flow into the input to amplifier 120 from the non-selected row electrodes.

Current only flows into the input of the amplifier 120 from the selected row electrode, which is held at a positive voltage by multiplexer 112. The magnitude of this current is determined by the resistance 140 between the row and column electrodes at the intersection currently addressed by multiplexers 112 and 116. This resistance, and hence the current into the amplifier, is determined by whether or not contact is made at the currently selected intersection. If no contact is made, the resistance is high, little current flows into the amplifier, and the amplifier output voltage remains at or close to zero. If contact is made, the interelectrode resistance switches to the low state, current flows into the amplifier input, and the output of the amplifier goes low. Thus, the operation of multiplexer 112, counter 114, and amplifiers 108 serve to isolate all but the selected selected intersection resistance from being measured as each column is selected by column multiplexer 116.

Figure 7:
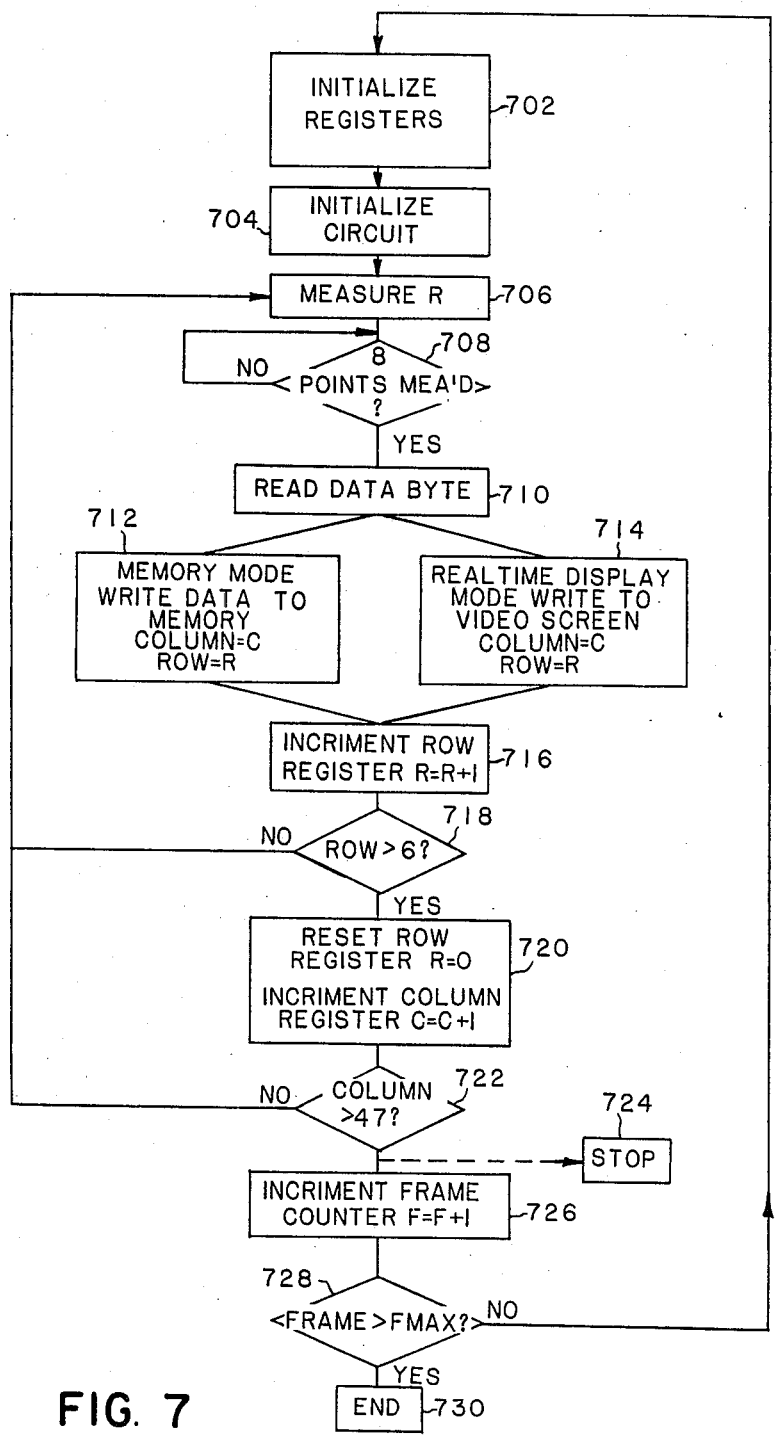
FIG. 7 shows one procedure by which a computer may control the circuitry of FIG. 6.

The procedure carried out by the computer 170 in reading the entire array will be described with reference to the flow diagram shown in FIG. 7 and the circuitry of FIG. 6.

To begin a measurement, the computer initializes the counters which keep track of the position for the measured data, block 702. In a real time display, the computer will zero or initialize counters repsenting the rows and columns of the display corresponding to the rows and columns of the sensor. If the data is to be stored, the computer will initialize registers designating the memory area where the data is to be stored.

Next, the computer sends signals to the measurement circuit of FIG. 6 which reset the row and column counters and begin the measurement process, block 704. This resets row counter 114 and cloumn counter 118 to their initial values, which are zero in the described embodiment. After this, the measurement process begins.

The processor sends a signal to the measurement circuitry which causes the circuitry to measure the resistance of the first eight points of the sensor array, block 706. The data is transferred to the computer in 8-bit bytes. While the measurement circuitry is measuring eight array points, the computer waits for a signal from the interface circuit indicating that the measurement is complete, block 708. During this period the measurement circuitry of FIG. 6 performs the following operations.

At the beginning of the measurement of the electrode array, row and column counters are set to zero. Multiplexer 116 applies the signal on the first column electrode $C_1$ to the threshold detector 122, and multiplexer 112 applies a high signal to the first row electrode $R_1$. The high or low voltage from multiplexer 116 indicates the resistance at the selected array point, and threshold detector 122 converts this to a digital value which is clocked into a register 130.

Register 130 is an 8-bit, addressable register. The 3 LSB's from the row counter are applied to the address inputs of register 130. Register 130 and row counter 114 are clocked by a signal from the interface circuit on line 136. The first clock pulse following the beginning of the measurement clocks the output from threshold detector 122 into the first bit of register 130 and also increments row counter 114.

The above procedure is repeated for each of the first eight array locations in the first column, with the value in row counter 114 being incremented after each point is measured to provide the proper row address to multiplexer 112 and the proper register address to 8-bit register 130. A busy signal corresponding to the 4th bit of the row counter is applied to the interface circuit 160 on line 138 and indicates when 8 array points have been measured and register 130 is ready to be read.

When the busy signal goes high, the computer goes to block 710 where the first eight bits of data are read into the computer. The computer either stores the data for later processing and display, block 712, or sends the data to a display such as a CRT screen for immediate viewing, block 714. The clock signal to the row counter and register 130 is disabled while the computer is reading the data. The computer then increments its internal row register, block 716, and checks to see whether all the columns in the rwo have been read, block 718. If not, the computer returns to block 706 where the above process is repeated, except that the MSB's of the row counter cuase multiplexer 112 to select the next eight rows of the array during the next processing of eight bits.

If all the data from a row has been read, the computer prepares to read the data from the next column by resetting its row register to 0 and incrementing the column register, block 720. The computer checks to see whether all columns have been read, block 722. If not, the computer returns to block 706, and the first eight bits of the next column are read. This procedure is repeated until data from all the points in the sensor array have been read into the computer.

If all columns have been read, and the computer is taking only one measurement of the patient's occlusion, the computer stops, block 724, until a request for another reading starts the above process again at block 702. Alternatively, the computer can take several occlusion measurements to show, for example, the change in occlusion as the patient's jaw closes. In this case, the computer increments a frame counter, block 726, which keeps track of which measurement is currently being taken. The computer then checks to see whether all the measurements to be taken are complete by comparing the frame counter with a maximum frame number, block 728. If the measurements are complete, the computer stops, block 730. Otherwise, the computer returns to block 702 where another measurement process is begun.

With the circuit shown in FIG. 6, the sensor and measurement circuitry are able to determine the resistance of an array point every 10 microseconds. With the 48 by 48 electrode array having 2304 array points, the fastest possible sampling speed is about 43 Hz. Using an IBM PC with the procedure and circuitry described, the actual sampling rate is about 33 Hz, or one complete measurement every 0.03 seconds. This rate is sufficiently fast to give excellent resolution in dynamically measuring a patient's occlusion to diagnose bite and dental problems.

There has been described a new and useful method, sensor, and circuitry for detecting contact points, and in particular for performing measurements of dental occlusion. It should be appreciated that the sensor described herein, while particularly suited to dental occlusion measurements, may be used in other situations where measurement of points of contact is desired, especially whre the measurement sensor must be extremly thin to avoid disturbance of the contact area being measured, and that this embodiment may be modified by those of ordinary skill in the art in applying the teachings of the invention in different applications and circumstances. Therefore, the invention should not be limited by the disclosure of particular circuitry or procedures herein, but rather the invention should only be interpreted in accordance with the following claims.

What is claimed is:

1. Apparatus for measuring a person's dental occlusion, comprising:
   a thin, flexible sensor, including:
      a plurality of flexible, generally parallel electrodes supported by a thin flexible backing sheet to provide a set of row electrodes;
      a second plurality of flexible, generally parallel electrodes supported by a thin flexible backing sheet to provide a set of column electrodes;
      a resistive layer between the row and column electrode sets made of a substantially homogeneous resistive material whose resistance changes as a function of the pressure applied thereto;
      means for positioning the row and column electrodes so that the two electrodes sets face one another separated by the resistive layer so as to form a thin, flexible sensor with the electrodes oriented so that the electrodes of one set cross the electrodes of the other set at an angle to create a plurality of intersections where row electrodes cross over column electrodes;
      said means for positioning being such as to allow insertion of the sensor into the person's mouth so that the facing electrode sets are between the person's upper and lower teeth; and
      terminal means for applying signals to each of the electrodes; and
   means connected to the terminal means for sensing the resistance between the respective row and column electrodes at each intersection and for providing an output in response thereto representative of the contacting points of the patient's bite.

2. The apparatus of claim 1 wherein the resistive layer includes a resistive coating made of said resistive material deposited over each of the row and column electrode sets.

3. The apparatus of claim 2 wherein the sensor includes a separation layer between the resistive coatings over the first and second electrode sets.

4. The aparatus of claim 3 wherein the resistive layer includes a resistive paint having titanium dioxide and graphite as components thereof.

5. The apparatus of claim 4 wherein the thickness of each of the resistive coatings is 2 mils or less.

6. The apparatus of claim 5 wherein the resistivity of the resistive paint is in the range of 40 to 100 kilohms per square for a 1 mil thickness.

7. The apparatus of claim 2 wherein the means for sensing includes:
   means for detecting whether the resistance between the first and second electrodes at each intersection is above or below a preselected threshold level.

8. The apparatus of claim 2 wherein the means for sensing includes:
   means for sequentially selecting individual electrodes from among the row electrodes and for applying a first potential to all row electrodes except the selected electrode;
   means for applying a second potential to the selected electrode; and
   means for measuring the resistance between each of the column electrodes and the selected row electrode during the time that each row electrode is selected.

9. The apparatus of claim 8 wherein the means for measuring includes means for comparing the voltage on a selected column electrode to a threshold voltage and for providing an output signal representative of whether the voltage on the selected electrode is above or below the threshold.

10. A method of measuring a person's dental occlusion, including the steps of:
    providing a plurality of flexible generally parallel electrodes supported by a thin flexible backing sheet to provide a set of row electrodes;
    providing a second plurality of flexible generally parallel electrodes oriented at an angle to the row electrodes and supported by a thin flexible backing sheet to provide a set of column electrodes;

arranging the row and column electrodes with the two electrodes sets facing one another, separated by a resistive layer made of a substantially homogeneous resistive material whose resistance changes as a function of the pressure applied thereto, and oriented so that the electrodes of one set cross the electrodes of one set cross the electrodes of the other set at an angle to create a plurality of intersections where row electrodes cross over column electrodes;

positioning the sensor in the person's mouth between the person's upper and lower teeth;

having the person bite down on the sensor; and sensing the resistance between the respective row and column electrodes at each intersection and providing an output in response thereto representative of the contacting points of the patient's bite.

11. The method of claim 10 wherein the step of arranging includes the step of applying a resistive coating over each of the sets of row and column electrodes.

12. The method of claim 11 wherein the step of sensing includes the step of detecting whether the resistance between the first and second electrodes at each intersection is above or below a preselected threshold level.

13. The method of claim 11 wherein the step of sensing includes the steps of:

sequentially selecting individual electrodes from among the row electrodes and applying a first potential to all row electrodes except the selected electrode;

applying a second potential to the selected electrode; and measuring the resistance between each of the column electrodes and the selected row electrode during the time that each row electrode is selected.

14. The method of claim 13 wherein the step of measuring includes the step of comparing the voltage on a selected column electrode to a threshold voltage and providing an output signal representative of whether the voltage on the selected electrode is above or below the threshold.

15. A thin, flexible contact sensor for sensing points of contact between two opposing objects, comprising:

a plurality of flexible, generally parallel electrodes supported by a thin flexible backing sheet to provide a set of row electrodes;

a second plurality of flexible, generally parallel electrodes supported by a thin flexible backing sheet to provide a set of column electrodes;

a resistive layer between the row and column electrode sets made of a substantially homogeneous resistive material whose resistance changes as a function of the pressure applied thereto;

means for positioning the row and column electrodes so that the two electrodes sets face one another separated by the resistive layer so as to form a thin, flexible sensor with electrodes oriented so that the electrodes of one set cross the electrodes of the other set at an angle to create a plurality of intersections where row electrodes cross over column electrodes, and so that the row and column electrodes so positioned can be inserted between the two opposing objects so that contact between the two objects is made through the backing sheets forcing the row and column electrodes closer to one another at said intersections through the resistive coating;

terminal means for applying signals to each of the electrodes; and means connected to the terminal means for sensing the resistance between the respective row and column electrodes at each intersection and for providing an output in response thereto representative of the contacting points between the opposing object including means for sensing contacting points occuring concurrently and for preventing false readings resulting from multiple contacting points occuring along each of a row electrode and a column electrode having a contacting point at the intersection therebetween.

16. The apparatus of claim 15 wherein the resistive layer includes a resistive coating made of said resistive material applied over each of the row and column electrode sets.

17. The apparatus of claim 16 wherein the sensor includes a separation layer between the resistive coatings over the first and second electrode sets.

18. The apparatus of claim 16 wherein the resistive coatings include a resistive paint having titanium dioxide and graphite as components thereof.

19. The apparatus of claim 18 wherein the thickness of the resistive coatings is 2 mils or less.

20. The apparatus of claim 18 wherein the resistivity of the resistive paint is in the range of 40 to 100 kilohms per square for a 1 mil thickness.

21. The apparatus of claim 16 wherein the means for sensing includes:

means for detecting whether the resistance between the first and second electrodes at each intersection is above or below a preselected threshold level.

22. The apparatus of claim 16 wherein the means for sensing includes:

means for sequentially selecting individual electrodes from among the row electrodes and for applying a first potential to all row electrodes except the selected electrode;

means for applying a second potential to the selected electrode; and means for measuring the resistance between each of the column electrodes and the selected row electrode during the time that each row electrode is selected.

23. The apparatus of claim 22 wherein the means for measuring includes means for comparing the voltage on a selected column electrode to a threshold voltage and for providing an output signal representative of whether the voltage on the selected electrode is above or below the threshold.

* * * * *